(12) United States Patent
Shekarriz et al.

(10) Patent No.: US 12,053,281 B2
(45) Date of Patent: *Aug. 6, 2024

(54) TRANSDERMAL SAMPLING STRIP AND METHOD FOR ANALYZING TRANSDERMALLY EMITTED GASES

(71) Applicant: Exhalix LLC, Albuquerque, NM (US)

(72) Inventors: Alireza Shekarriz, Cle Elum, WA (US); Debra May Friedrichsen, Corvallis, OR (US)

(73) Assignee: Exhalix LLC, Rio Rancho, NM (US)

( * ) Notice: Subject to any disclaimer, the term of this patent is extended or adjusted under 35 U.S.C. 154(b) by 617 days.

This patent is subject to a terminal disclaimer.

(21) Appl. No.: 16/952,300

(22) Filed: Nov. 19, 2020

(65) Prior Publication Data

US 2021/0068719 A1 Mar. 11, 2021

Related U.S. Application Data

(63) Continuation of application No. 15/542,413, filed as application No. PCT/US2016/012577 on Jan. 8, 2016, now Pat. No. 10,856,790.

(60) Provisional application No. 62/101,821, filed on Jan. 9, 2015.

(51) Int. Cl.
 *A61B 5/1477* (2006.01)
 *A61B 5/145* (2006.01)
 *A61B 10/00* (2006.01)
 *G01N 33/49* (2006.01)

(52) U.S. Cl.
 CPC ........ *A61B 5/1477* (2013.01); *A61B 5/14507* (2013.01); *A61B 5/14542* (2013.01); *A61B 5/14546* (2013.01); *A61B 10/00* (2013.01); *A61B 10/0064* (2013.01); *A61B 2010/0083* (2013.01); *A61B 2560/0412* (2013.01); *G01N 33/4925* (2013.01)

(58) Field of Classification Search
 CPC .............. A61B 5/1477; A61B 5/14507; A61B 5/14542; A61B 5/14546; A61B 2010/0083; A61B 2560/0412; G01N 33/4925
 See application file for complete search history.

(56) References Cited

U.S. PATENT DOCUMENTS

| | | |
|---|---|---|
| 4,005,700 A | 2/1977 | Parker |
| 4,274,418 A | 6/1981 | Vesterager |
| 4,836,907 A | 6/1989 | Pedersen |
| 5,628,310 A | 5/1997 | Rao |

(Continued)

FOREIGN PATENT DOCUMENTS

| | | |
|---|---|---|
| EP | 2685231 A | 1/2014 |
| EP | 3006915 A | 4/2016 |

(Continued)

OTHER PUBLICATIONS

Schiavon et al, Anal. Chem 1995, 67, 318-323.

*Primary Examiner* — David J. McCrosky (57) ABSTRACT

Transdermally emitted gasses are detected by applying a dermal sampling strip to the skin of a biological subject, capturing the gasses in a vapor space in the dermal sampling strip, and analyzing for at least one such gas captured in the vapor space of the dermal sampling strip. Analysis is preferably performed using an electrocatalytic cell, which can be mounted on the dermal sampling strip and form a wall of the vapor space.

4 Claims, 2 Drawing Sheets

(56) References Cited

U.S. PATENT DOCUMENTS

| | | | |
|---|---|---|---|
| 5,944,661 | A | 8/1999 | Swette |
| 7,266,404 | B2 | 9/2007 | Tsuda |
| 7,474,908 | B2 | 1/2009 | Gisiger |
| 7,811,276 | B2 | 10/2010 | O'Neill |
| 7,862,698 | B2 | 1/2011 | Haener |
| 8,048,677 | B2 | 11/2011 | Hansen |
| 8,386,027 | B2 | 2/2013 | Chuang |
| 8,398,199 | B2 | 3/2013 | Kamiyama |
| 8,527,023 | B2 | 9/2013 | Hayoz |
| 2005/0096513 | A1 | 5/2005 | Ozguz |
| 2007/0083094 | A1 | 4/2007 | Colburn |
| 2013/0123589 | A1* | 5/2013 | Moritani .............. A61B 5/1451 600/309 |
| 2013/0281806 | A1 | 10/2013 | Rao |
| 2016/0120458 | A1 | 5/2016 | Yamada |

FOREIGN PATENT DOCUMENTS

| | | |
|---|---|---|
| JP | 2014-157125 A | 8/2014 |
| WO | WO89/04630 A | 6/1989 |
| WO | 2014/192674 A | 12/2014 |

\* cited by examiner

TRANSDERMAL SAMPLING STRIP AND METHOD FOR ANALYZING TRANSDERMALLY EMITTED GASES

CROSS REFERENCE TO RELATED APPLICATIONS

This application is a continuation of application Ser. No. 15/542,413, filed 7 Jul. 2017, which is a § 371 of PCT/US2016/012577, filed 8 Jan. 2016, which claims benefit of U.S. Provisional Patent Application No. 62/101,821, filed 9 Jan. 2015.

STATEMENT REGARDING FEDERALLY SPONSORED RESEARCH OR DEVELOPMENT

Not applicable.

NAMES OF THE PARTIES TO A JOINT RESEARCH AGREEMENT

Not applicable.

INCORPORATION BY REFERENCE OF MATERIAL SUBMITTED ON A COMPACT DISC OR AS A TEXT FILE VIA THE OFFICE ELECTRONIC FILING SYSTEM (EFS-WEB)

Not applicable.

STATEMENT REGARDING PRIOR DISCLOSURES BY THE INVENTOR OR A JOINT INVENTOR

Not applicable.

BACKGROUND OF THE INVENTION

Field of the Invention

Body fluids such as blood, urine and even breath are routinely analyzed for medical, diagnostic and legal reasons. Among the many analytes that are examined there are a number of small molecules like carbon dioxide ($CO_2$), oxygen ($O_2$), nitric oxide (NO), nitric dioxide ($NO_2$), hydrogen peroxide ($H_2O_2$), acetaldehyde ($C_2H_4O$), carbon monoxide (CO), ammonia ($NH_3$), hydrogen sulfide ($H_2S$), acetone ($C_3H_6O$), hydrogen cyanide (HCN), and formaldehyde ($CH_2O$) that have been associated with various diseases or conditions. Breath analysis is interesting because it is non-invasive, but in the case of trace gases such as $H_2S$ and $NH_3$, the concentrations of these compounds in exhaled air are too low to be analyzed easily and inexpensively. This is further complicated by the presence of bacteria in the respiratory system, moisture, and reactions that can occur.

Analysis for $H_2S$ is of interest because the serum concentration of $H_2S$ correlates with the risk of peripheral artery disease (PAD) and other cardiovascular disease. Excess $H_2S$ is toxic and plasma concentrations above 20 µM cause mitochondrial poisoning and cell death. Therefore, a way to quickly and accurately estimate serum $H_2S$ levels can be an important diagnostic tool.

Some molecules are emitted transdermally. In principle, the capture and analysis of these transdermally emitted molecules has diagnostic or investigative value, and there have been attempts to develop devices, which accomplish this.

U.S. Pat. Nos. 4,274,418, 4,005,700, 4,836,907, 7,474,908, 8,048,677, 8,527,023, and 7,862,698 describe devices comprising a body having a gas-permeable boundary wall for placement on the skin of the subject, a gas collection chamber in the body connected to an analysis instrument, a heating device to heat the skin area under the boundary wall and an electronic control to control the heating device and monitor the temperature of the skin area.

WO 2012/45047 describes an apparatus including a diffusion chamber adapted to receive an appendage of the patient; a measuring chamber pneumatically coupled to the diffusion chamber adapted to receive at least a portion of one or more analytes from the diffusion chamber; at least one optical sensor positioned in the measuring chamber, and at least one optoelectronic component positioned outside of the measuring chamber for the remote detection of chemical interaction and/or physical interaction of the at least one optical chemical sensor.

U.S. Pat. No. 5,628,310 discloses an apparatus and method to enable minimally invasive transcutaneous measurements through fluorescence lifetime monitoring of an implanted element.

U.S. Pat. No. 8,386,027 discloses a device that contains (i) a hand piece, (ii) an abrasive tip, (iii) a feedback control mechanism, (iv) two or more electrodes, and (v) an electrical motor.

Other devices are described in U.S. Pat. Nos. 7,811,276, 8,393,199, 7,266,404 and U.S. Patent No. 2007-0083094.

BRIEF SUMMARY OF THE INVENTION

The invention in one aspect is a method for measuring the transdermal emission of a gas through the skin of a biological subject, comprising a) sealably mounting at least one dermal sampling strip on the skin of the subject, wherein the dermal sampling strip includes a sample collection chamber that comprises (i) a skin contact side that is in contact with the skin when the dermal sampling strip is mounted and (ii) one or more walls, the skin contact side and the wall(s) together defining a vapor space for collecting transdermally emitted gas, wherein the skin contact side has one or more openings which create one or more fluid paths between the skin and the vapor space for collecting the transdermally emitted gas;

b) collecting the transdermally emitted gas in the sample collection chamber of the dermal sampling strip(s); and c) analyzing for at the presence of at least one component of the transdermally emitted gas collected in the sample collection chamber of the dermal sampling strip(s) by contacting the transdermally emitted gas with a working electrode of an electrocatalytic cell, and measuring an electrical signal created by a reaction of the at least one component of the transdermally emitted gas at the working electrode.

In another aspect the invention is a method for measuring the transdermal emission of a gas through the skin of a biological subject, comprising a) sealably mounting at least one dermal sampling strip on the skin of the subject, wherein the dermal sampling strip includes a sample collection chamber that comprises (i) a skin contact side, (ii) one or more walls, the skin contact side and the wall(s) together defining a vapor space for collecting transdermally emitted gas, and wherein the skin contact side has one or more openings which create one or more fluid paths between the skin and the vapor space for collecting the transdermally emitted gas, to form a seal between the skin and the sample collection chamber and such that the skin contact side of the dermal sampling strip is in contact with the skin b) collecting the transdermally emitted gas in the sample collection chamber of the dermal sampling strip(s); and c) analyzing the transdermally emitted gas collected in the sample collection chamber of the dermal sampling strip(s) for the presence of at least one component selected from nitric oxide, nitric dioxide, hydrogen peroxide, acetaldehyde, carbon monoxide, ammonia, hydrogen sulfide, acetone, hydrogen cyanide and formaldehyde.

In a third aspect, the invention is a transdermal gas analyzer comprising a) a dermal sampling strip that includes a sample collection chamber that includes (i) a skin contact side and (ii) one or more walls, the skin contact side and the wall(s) together defining a vapor space for collecting transdermally emitted gas, and wherein the skin contact side has one or more openings which create one or more fluid paths between the skin and the vapor space for collecting the transdermally emitted gas, b) a detector for detecting the presence of one or more components of the transdermally emitted gas collected in the vapor space of the sample collection chamber, wherein the detector is in fluid communication with the vapor space such that a fluid path is defined from the skin to the detector such that the transdermally emitted gas is transported through the fluid path from the skin to the detector without passing through a diffusion barrier.

In a fourth aspect, the invention is a dermal sampling strip comprising a sample collection chamber, a detector and electrical contacts for connecting the detector to a power source that provides electrical power to the detector, wherein:

the sample collection chamber comprises (i) a skin contact side and (ii) one or more non-porous walls, the skin contact side and the non-porous wall(s) together defining a vapor space for collecting transdermally emitted gas, and wherein the skin contact side has one or more openings which create one or more fluid paths between the skin and the vapor space for collecting the transdermally emitted gas; and the detector forms or is mounted onto at least one of the walls of the sample collection chamber and is in fluidic communication with the vapor space of the sample collection chamber.

DETAILED DESCRIPTION OF THE INVENTION

Figure 1:
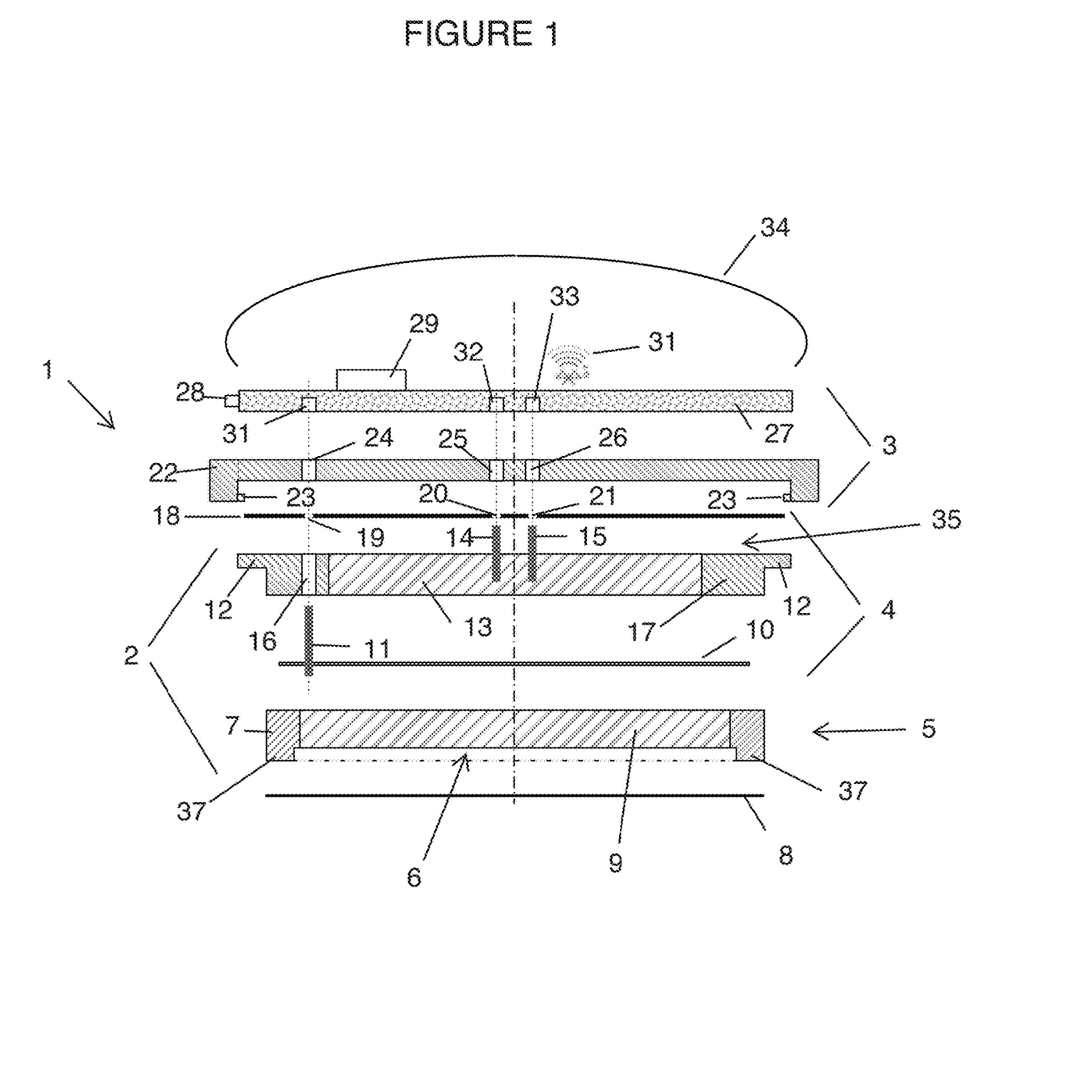
FIG. 1 is an exploded cross-sectional side view of an embodiment of a transdermal gas analyzer of the invention.

In FIG. 1, transdermal gas analyzer 1 includes dermal sampling strip 2, electronics module 3, optional removable protective film 8 and optional protective covering 34. Instead of or in addition to protective covering 34, the entire device may be incorporated into a housing. Alternatively, dermal sampling strip 2 and electronics module 3 may be incorporated into separate housings, which may include means for removably and replaceably attaching dermal sampling strip 2 to electronics module 3.

In the embodiment shown in FIG. 1, dermal sampling strip 2 includes sample collection chamber 5. Sample collection chamber 5 includes peripheral walls 7 and working electrode 10, and skin side 6 which together define vapor space 9. As shown, skin side 6 is open, forming a fluid path between vapor space 9 and the skin of a subject to which dermal sampling strip 2 is applied. In this embodiment, working electrode 10 forms a wall of sample collection chamber 5.

If desired, skin side 6 of sample collection chamber 5 may be covered with a screen, porous film or other layer (not shown) that defines multiple openings that form fluid paths between vapor space 9 and the skin.

Similarly, vapor space 9 of sample collection chamber 5 may be partially or entirely filled with a porous material (such as a resilient polymer foam that has at least 50% open and interconnected cells) and/or a particulate solid, provided that such porous material and/or particulate solid permits bulk gas transport from the skin through vapor space 9 and to detector 4. The presence of such porous material and/or particulate solid provides a physical barrier between the skin of the biological subject and the walls of sample collection chamber 5, and in particular any detector 4 which is mounted onto or forms a wall or walls of sample collection chamber 5. If a porous material is present, it is most preferably a rigid or semi-rigid polymeric foam. The polymeric foam may be a reticulated foam in which cell windows are absent. The fluid path from the skin through vapor space 9 to detector 4 does not contain any liquid, gel, membrane or other solid material which presents a diffusion barrier (i.e., prevents bulk transport by requiring an emitted gas to permeate through a liquid, gel or semi-permeable membrane) to a transdermally emitted gas that enters vapor space 9.

In some embodiments vapor space 9 of sample collection chamber 5 may contain a sorbent or other fixative for one or more transdermally emitted gasses. This permits such gas or gasses captured in vapor space 9 and to be analyzed using a separate detector, i.e., one that does not reside on dermal sampling strip 2 or transdermal gas analyzer 1, by removing the sorbent and the gas captured on or in it. The use of a sorbent or fixative also can prevent one or more components of the transdermally emitted gas from reaching detector 4, while allowing one or more other components of the gas to reach detector 4. This can be useful, for example, to prevent interference and/or to isolate the signal produced at detector 4 by one or more specific target gases.

By "sorbent" or "fixative", it is meant some structure that binds a transdermally emitted gas to the sorbent or fixative. The binding mechanism may be mechanical. For example, cells of a polymeric foam or other porous material can mechanically capture molecules of the transdermally emitted gas. The binding mechanism also can be chemical and/or physiochemical. A chemical sorbent or fixative engages in a chemical reaction with a transdermal gas to bind the gas or some reaction product thereof to the sorbent or fixative. In the case of $H_2S$, for example, a chemical sorbent may include one or more materials that are reactive with $H_2S$ molecules, including, for example, metal ions (including alkali metal ions and/or salts thereof and transition metal compounds such as hydrated iron (III) oxide), alcohol groups, isocyanate groups, epoxide groups, chlorine or chlorine precursor and the like. A physiochemical sorbent or fixative absorbs and/or adsorbs a transdermally emitted gas through a physisorption and/or chemisorption mechanism. Examples of sorbent or fixative materials include various forms of carbon, including carbon black, activated carbon, graphite, expanded graphite, carbon nanotubes and the like; molecular sieves, including zeolites; various high-surface area mineral powders, sorbent gels such as polymethylsiloxane polyhydrate, and the like.

In the embodiment shown, working electrode 10 of detector 4 is integrated into sample collection chamber 5 and forms a wall thereof. This is an optional feature. Alternatively, for example, a separate wall structure (not shown) may be interposed between detector 4 and vapor space 9, such that vapor space 9 is defined by peripheral walls 7 and the separate wall structure. In such a case, the separate wall structure preferably includes one or more openings through which transdermally emitted gas captured in vapor space 9 can pass through to detector 4. Any such separate wall structure should not form or include a diffusion barrier.

The volume of vapor space 9 may be, for example, at least 10 $mm^3$, at least 100 $mm^3$ or at least 250 $mm^3$, up to 100 $cm^3$, up to 25 $cm^3$, up to 10 $cm^3$ or up to 1 $cm^3$. The height (dimension transverse to the skin when mounted) of vapor space 9 may be, for example, 0.5 mm to 2.54 cm, 0.1 to 1 cm or 0.1 to 0.5 cm. The internal transverse dimensions of sample collection chamber 5 (i.e., perpendicular to the thickness) each may be, for example, 0.5 to 25 cm or 2 to 15 cm, at their widest point. The cross-sectional area of vapor space 9 (transverse to its height) may be, for example, 25 $mm^2$ to 625 $cm^2$, or 400 $mm^2$ to 250 $cm^2$. Vapor space 9 may have any convenient cross-sectional shape, such as a circle, ellipse, rectangle, square, other polygon, or other shape.

The materials of construction of peripheral walls 7 and any separate wall structure may be any non-porous material that is sufficiently impervious to gas to allow gases emitted from the skin of the biological subject to be captured and held in vapor space 9 of sample collection chamber 5. Suitable materials of construction may include one or more of the various organic polymers including Teflon, polycarbonate, polyethylene, polypropylene, polystyrene, polyimide, acrylonitrile-butadiene-styrene (ABS), high impact polystyrene (HIPS), nylon, fluoroelastomer and fluoro-rubber, various polyurethanes, etc., as well as materials such as paper or other cellulosic materials and non-reactive metals.

Sample collection chamber 5 may include various optional features. One such optional feature is internal structure that creates a flow path of transdermally emitted gas within vapor space 9 of sample collection chamber 5. An example of such internal structure is, for example, a series of raised ridges that produce one or more channels within vapor space 9, thus defining a fluid flow path. Such a fluid flow path may be useful, for example, in efficiently transporting transdermally emitted gases to detector 4, and/or for transporting transdermally emitted gases out of sample collection chamber 5 for remote analysis.

Sample collection chamber 5 may include one or more gas inlet ports or header, into which a gas can be introduced into vapor space 9, and/or one or more gas outlet ports or header, from which the sample or other gas can be withdrawn from vapor space 9. A gas inlet port and gas outlet port each may be, for example, a solenoid valve or another type of valve, or a septum port, or the like. Such inlet and outlet ports are useful for retrieving or recovering a captured transdermally emitted gas from vapor space 9 of sample collection chamber 5 for remote analysis. Such inlet and/or outlet ports can communicate with one or more channels formed by internal structure within vapor space 9 of sample collection chamber 5, such that a serpentine flow path is established from a gas inlet port to a gas outlet port. Arrangements such as these provide a means for efficient recovery of captured emitted gases from vapor space 9 and elimination of flow recirculation or dead zones within vapor space 9. Upon opening a gas outlet port, captured emitted gasses can be withdrawn from sample collection chamber 5 for remote analysis. A gas inlet port is generally opened during sample removal to facilitate flow of the captured gasses. A carrier or purge gas such as nitrogen or argon can be introduced through a gas inlet port to push the trapped emitted gasses out of vapor space 9 of sample collection chamber 5. Alternatively, in certain circumstances, a vacuum can be drawn through a gas outlet port to remove the captured transdermally emitted gasses and replace the removed gasses with clean atmospheric gas.

In the embodiment shown in FIG. 1, detector 4 is an electrocatalytic cell 35 that, as shown, includes working electrode 10, counter electrode 14, optional but preferred reference electrode 15 and electrolyte 13. Counter electrode 14, reference electrode 15 and electrolyte are contained within housing 17. Working electrode 10, counter electrode 14 and reference electrode 15 are in contact with electrolyte 13, but not in direct contact with each other. In the embodiment shown, electrically conductive contact 11 extends through via sealed thru hole 16 of housing 17, and connects to contact terminal 31 of electronics module 27.

Electrocatalytic cell 35 is designed and operated such that, when in the presence of at least one target molecule, i.e., at least one transdermally emitted gas, it creates a signal (typically an electrical or electromagnetic signal) that indicates qualitative and/or quantitative presence of such gas or gas molecules. The target molecule in some aspects is selected from one or more of carbon dioxide, oxygen, nitric oxide, nitric dioxide, hydrogen peroxide, acetaldehyde, carbon monoxide, ammonia, hydrogen sulfide, acetone, hydrogen cyanide and formaldehyde. In the embodiment shown in FIG. 1, the captured transdermally emitted gas (including the target molecule) is brought into contact with working electrode 10, which is typically the anode of electrocatalytic cell 35. A voltage is applied to working electrode 10. Electrochemical reactions of the transdermal gas at the surface of working electrode 10 indicate the presence of the transdermal gas qualitatively and/or quantitatively.

Electrochemical methods for detecting $H_2S$ are described, for example, by Pandey et al., "A review of sensor-based methods for monitoring hydrogen sulfide", *Trends in Analytical Chemistry* 2012 32:87-99, Hodgson et al., "Amperometric Gas Sensors with Detection Limits in the Low ppb Range", *Analytica Chemica Acta* 1999, 393:43-48; and Yu et al., "Electrochemical $H_2S$ Sensor with $H_2SO_4$ Pre-Treated Nafion Membrane as Solid Polymer Electrolyte," *Sensors and Actuator* B 86 (2002) 259-265.

The working electrode of the electrocatalytic cell typically is at least one metal surface at which an electrocatalytic reaction of a target molecule takes place. The working electrode may be created by coating or otherwise depositing a metal onto a polymeric base. The metal is one that catalyzes a reaction that, depending on the particular target analyze molecule, may be an oxidation or reduction reaction, of the target molecule at the metalized electrode surface. Preferred metals are gold, silver, copper, lead and platinum, with gold being of particular interest. The metal may be in a microcrystalline state. The metal may also adsorb the target analyte molecule from the gas captured in vapor space 9.

The working electrode is also preferably permeable to water and hydrogen or other ions, particularly cations and protons that may be produced in the reaction of the target molecule. In a preferred working electrode, the metal is coated or otherwise deposited onto a solid, semi-permeable membrane. The membrane may be an organic polymer. An example of a membrane material is an ionomer film such as a sulfonated fluoropolymer film (or other cation-exchange membrane that has multiple anionic groups (such as strong or weak acid groups)). Such films are available commercially as Nafion® films. Other membrane materials of interest include anion-exchange membranes that have multiple cationic groups, including Selemion™ anion exchange membranes sold by Asahi Glass.

The working electrode and/or its polymeric membrane base may be roughened, deformed, or embossed to have microstructures such as micropins, riblets, grooves, or corrugations to provide a higher exposed surface area for better adhesion of the metal (electrocatalytic) surface and reaction with target analyte molecules. The plated metal preferably has a somewhat roughened surface as typically appears when the deposited metal is in a microcrystalline state. The plated metal may have some discontinuities, in the form of pores, cracks or the like which allow small molecules or ions to pass through the plated metal during the reaction of the target molecule, as needed to complete the reaction.

A suitable method for plating a polymer membrane with gold or other metal is described, for example, in Jordan and Hauser, *Anal. Chem.* 69, 558-562, 1997, and Cook, *Journal of the Electrochemical Society,* 235, 187-189, 1990. In general, a film of the polymer is bathed in a solution of a soluble metal compound, typically a halide or a sulfide, to absorb the metal compound onto the film surface. The absorbed metal compound is reduced at the surface of the polymer film by contacting the polymer film with a reducing solution. In preferred cases in which the polymer film is semi-permeable, the film can be used to divide a cell into two sections, one of which contains the metal compound solution and one of which contains the reducing agent solution. In this manner, the polymer film can be bathed in both solutions simultaneously, with the plating reaction occurring on or within the polymer film. Suitable metal compounds are halides of the metal to be plated, such as silver chloride, copper chloride, gold chloride, lead chloride, gold hydrogen chloride ($HAuCl_4$) and the like. Suitable reducing agents include borohydride salts such as sodium borohydride and sodium bisulfite. These solutions can be stabilized by adjusting their pH into the basic range such as by addition of caustic. A preferred deposition temperature is 5 to 30° C., especially 10° C. and 20° C.

Working electrode 10 may be supported if necessary to minimize or eliminate flexing during operation. Flexing or other movement of the anode may lead to inaccuracies or variations in the current produced during operation of the sensor. For example, working electrode 10 can be supported on its upper and/or lower surface, or may be sandwiched between two supporting plates. Any supporting plate on the side of working electrode 10 that faces vapor space 9 of sample collection chamber 5 preferably is porous so that the target gas can permeate them and reach the electrode surface without blocking the reaction surface. A supporting plate on the opposing side of working electrode is similarly porous, to permit contact with electrolyte 13. Such supporting plate or plates tend to immobilize working electrode 10, reducing or preventing deflections due to pressure fluctuations and mechanical shock, which could otherwise result in noisy and shifting sensor outputs.

Working electrode 10 is in contact with electrolyte 13. Electrolyte 13 may be liquid, solid or a gel electrolyte. The electrolyte is capable of transporting ions from working electrode 10 to counter electrode 14 (and reference electrode 15 if present) of electrocatalytic cell 35. A suitable electrolyte is an aqueous solution that contains a mineral acid such as sulfuric or hydrochloric acid, such as a solution of 0.01 to 5 M sulfuric acid, perchloric acid, or hydrochloric acid, although solutions of other mineral acids and even organic acids are suitable. Solid and gel electrolytes are also useful. Electrolyte 13 may be sealed within a case, housing or other system, which prevents leakage and isolates the electrolyte from the outside environment. Such a cell housing may include a venting means, by which gasses can enter and exit the cell to balance pressures. The venting means should be substantially impermeable to the electrolyte so leakage does not occur. A suitable venting means is a small window of a gas-permeable membrane in the housing of the cell. A suitable gas-permeable membrane is a polytetrafluoroethylene polymer such as a Gore-Tex membrane, or similar type of hydrophobic membrane. The cell housing can also function as the working electrode, counter electrode and/or reference electrode, if the case is sufficiently electrically conductive.

In some embodiments, the working electrode and counter electrode (and preferably the reference electrode as well) are coated or otherwise deposited onto a porous membrane, provided that the electrodes are separated from each other. The polymeric membrane has ionic groups. The counter and reference electrodes may be coated or otherwise deposited onto the side of such a porous membrane opposite of the working electrode. The polymeric membrane in such cases can form all or part of the electrolyte of the electrocatalytic cell, and/or hold some or all of the electrolyte within pores in the polymeric membrane. Such a design has advantages in that the electrocatalytic cell can be made very thin and flexible. This facilitates incorporation into the dermal sampling strip, particularly when the dermal sampling strip is designed to be for single- or limited-use and therefore disposable.

When the electrodes are arranged on a polymeric membrane as just described, it may be beneficial to include an additional reservoir or electrolyte fluid or gel, in fluid communication with the polymeric membrane, to prevent the polymeric membrane from drying out. This can be mounted on the dermal sampling strip itself, and/or otherwise onto the transdermal gas analyzer of the invention.

Electrocatalytic cell 35 preferably also includes reference electrode 15 against which the potential of working electrode 10 is measured.

Counter electrode 14 and reference electrode 15 can be made of any conductive material, and may be made of the same metal as working electrode 10. Other materials used maybe graphite, stainless steel, or gold. Counter electrode 14 and reference electrode 15 are in electrical contact with electrolyte 13 but not in electrical contact with each other or with working electrode 10, except through electrolyte 13. Alternatively, the counter and reference electrodes maybe deposited, using for example a chemical vapor deposition approach, on the opposite side of the working electrode polymeric base, whereby the electrocatalyst (working electrode) is separated from the counter electrode and reference electrode by the thickness of the membrane.

Alternatively, other detectors can be used in place of or in addition to the electrocatalytic cell illustrated in FIG. 1, the detector being in the most general sense any device or substance that analyzes for at least one component of the transdermally emitted gas. Such component may be selected from one or more of carbon dioxide, oxygen, nitric oxide, nitric dioxide, hydrogen peroxide, acetaldehyde, carbon monoxide, ammonia, hydrogen sulfide, acetone, hydrogen cyanide and formaldehyde. "Analyzes" and its cognates for purposes of this invention refer to any method for qualitatively (and preferably quantitatively) determining the presence of the emitted gas. The particular method of analysis will of course be selected in connection with the specific transdermally emitted gas(ses) being analyzed for. Examples of useful detectors for performing various analytical methods therefore include, for example, gas chromatographs, mass spectrometers, atomic absorption spectrometers, atomic emission spectrometers, atomic fluorescence spectrometers, various colorimeters (including devices that detect variations in surface reflectivity or absorptivity), infrared spectrometers, gel permeation chromatographs, liquid chromatographs, raman spectrometers, x-ray fluorescence spectrometers, various chemical-based detectors and various electrochemical methods. The detector is selected to provide qualitative and preferably quantitative analysis of the target transdermally emitted gas(ses) in the concentration that accumulate in the sample collection chamber during the sampling period. The detector in some embodiments may be material that engages in a chemical reaction with the transdermal gas, producing a sensible change (for example, in appearance, odor, etc.) that indicates the presence of the transdermal gas. In some cases, sorbent and/or fixative materials described above may exhibit such a sensible change upon contact with the transdermal gas, and will also function as a detector.

Multiple detectors may be included in the transdermal gas analyzer. If multiple detectors are present, they may be of the same type, or may be of two or more different types.

The detector or a portion thereof may reside on dermal sampling strip 2 itself, as shown in FIG. 1. In such embodiments, at least one detector resides on dermal sampling strip 2, within or in fluid contact with vapor space 9 of sample collection chamber 5. As before, the detector or part thereof may form or be mounted onto a wall of collection chamber 5 that defines vapor space 9. In such embodiments, the captured transdermally emitted gas is brought into contact with the detector, which indicates the presence of the transdermally emitted gas (if simply qualitative) and/or the quantity thereof (if also quantitative).

In the embodiment shown in FIG. 1, detector 4 and sample collection chamber 5 collectively form dermal sampling strip 2. FIG. 1 illustrates a preferred embodiment in which dermal sampling strip 2 is removably and replaceably attached to electronics module 3. In such embodiments, means are provided to removably and replaceably attaching dermal sampling strip 2 to electronics module 3. In FIG. 1, such means are hooks 23 of electronics module support 3, which "snap" over corresponding flanges 12 of housing 17 and affix electronics module 3 to dermal sampling strip 2. Dermal sampling strip 2, flanges 12 and/or housing 17 are in such embodiments made of a flexible material that reversibly deform slightly under pressure to permit flanges 12 to fit under hooks 23.

Other suitable means for removably and replaceably attaching dermal sampling strip 2 to electronics module 3 include, for example, mechanical fasteners such as clips, snapping closures, screw-type closures, post-and-slot mechanisms and other mechanical closures; magnetic fasteners, and various types of adhesives.

The dermal sampling strip of the invention (as well as the transdermal gas analyzer as a whole) preferably is non-invasive, i.e., lacks any features that penetrates and/or punctures the skin of the subject when the dermal sampling strip is applied and used in the manner described herein.

In especially preferred embodiments, the dermal sampling strip of the invention is flexible and bends to conform to the surface of the skin of the biological subject to form a seal between the skin and the sample collection chamber.

In the embodiment shown in FIG. 1, electronic module 3 includes electronic circuitry 27, which houses the electronic components of transdermal gas analyzer 1, and optional module support 22.

Circuitry 27 includes the electronic components of transdermal gas analyzer 1. Circuitry 27 is in electrical contact with detector 4. In some embodiments, circuitry 27 includes circuitry for delivering electrical power from an electrical power source to detector 4, although this may not be necessary in embodiments in which detector 4 is not powered. Circuitry 27 may receive one or more electrical signals from detector 4, at least one of which is typically indicative of the qualitative and/or quantitative presence of one or more components of a transdermally emitted gas captured in vapor space 9 of sample collection chamber 5. Thus, circuitry 27 may include circuitry for receiving and analyzing an electrical signal produced by detector 4 in response to the presence of at least one transdermally emitted gas, such as one or more gases selected from carbon dioxide, oxygen, nitric oxide, nitric dioxide, hydrogen peroxide, acetaldehyde, carbon monoxide, ammonia, hydrogen sulfide, acetone, hydrogen cyanide and formaldehyde.

In the specific embodiment shown in FIG. 1, electrical power is supplied from circuitry 27 to electrocatalytic cell 35 via one or more of electrical contacts 31, 32 and 33, which are (when the device is assembled) in electrical contact with contact 11 of working electrode 10, counter electrode 14 and reference electrode 15, respectively. Vias 16, 19, 20, 21, 24, 25 and 26 extend through optional seal layer 18 and module support 22, permitting contact 11, counter electrode 14 and reference electrode 15 to make electrical contact with contact terminals 31, 32 and 33 of circuitry 27.

In embodiments such as shown in FIG. 1, in which detector 4 is an electrocatalytic cell, circuitry 27 preferably includes means for applying a predetermined electrical voltage to working electrode 10, and means for measuring electrical conditions (typically current) produced when the target molecule reacts at working electrode 10. A simple galvanometer or potentiostat is suitable for accomplishing both of these functions. Preferred devices are capable of imposing a potential having an amplitude (positive or negative) from 0.1 to 2.5, especially from 0.5 to 1.5 volts, to the working electrode, relative to a standard hydrogen electrode (SHE), and of measuring current amplitudes in the range of from 1 nA to 100 mA, especially from 0.1 µA to 1 mA. The circuitry may be, for example, an analog circuit that uses a pair of op amps, one as a biased emitter follower to provide the desired potential to the cell, and the other as a signal amplifier to measure the current produced by the cell. The circuitry may include one or more digital controllers, which facilitates real-time control of the applied voltage, baseline offsets and signal amplifier gain.

A number of commercially available galvanometers and potentiostats are useful. An example of a potentiostat with equally suitable performance is a Model 273-A potentiostat/galvanostat from Princeton Applied Research, Oak Ridge, Tenn., operated with CorrWare software (from Scribner Associates, Southern Pines, North Carolina). Another suitable example of a potentiostat is a Custom Sensor Solutions model 1401.

Circuitry 27 may include at least one human-readable display which, in response to the electrical conditions created by the oxidation or reduction of a target chemical at the working electrode, indicates the presence or absence of the target chemical in measurable quantities in the sample gas and/or the concentration of such target chemical in the sample gas. The display can be a visual type, a sonic type or some other suitable type. Combinations of various types can be used. A simple type of display is a light, such as an LED, which can be turned off or on (or display different colors) in response to the current produced when the target chemical is detected by detector 4, to indicate the presence or absence of the target molecule. For example, such a light can be set to be "off" until a target molecule is detected, in which case it becomes activated. A more complex display can be an LCD display or other graphical user interface, which can be designed to indicate the qualitative presence or absence of the target molecule, or which can provide quantitative information as to the concentration of target molecule in the sample gas stream.

Circuitry 27 also preferably includes an electrical power source and/or means for connection to an electrical power source, such as a cord, wiring and/or plug, or a port for receiving such a cord, wiring or plug. A suitable electrical power source is a direct current source such as battery 29, but an AC source in combination with a transformer (to produce DC power) can also be used.

Circuitry 27 may further include one or more communication modules 30 that are operable to communicate information (including data obtained from detector 4) to a remote device for, e.g., analysis and/or display and/or to receive communications from a remote device. Such a communication module may include one or more wireless communications devices that transmit an electromagnetic signal according to, for example the Bluetooth protocol, the IEEE 802.11 protocol (Wi-Fi), or via a cellular telephone protocol. Alternatively or in addition, a communication module may be adapted to deliver and/or receive a communication signal over a wire or cable, such as by delivering the signal to a communication port such as a USB port, HDMI port, optical cable port or other port 28 mounted onto circuitry 27.

Circuitry 27 may further include one or more user interfaces and/or controls, which may be graphical and/or mechanical, to permit a user to operate transdermal gas analyzer 1, and/or monitor or control its operation.

Circuitry 27 may also include various auxiliary electronic and/or electrical components, including but not limited to one or more microprocessors for operating the various other electronic components or the device as a whole.

Although shown in FIG. 1 as a single device, circuitry 27 may consist of two or more discrete modules, each of which contains one or more of the components described above.

Other optional features shown in FIG. 1 include protective covering 34, which may be transparent, rim 37 and removable protective film 8, which seals the opening(s) on skin side 6 of sample collection chamber 5 until the device is ready for use, at which time protective film 8 is removed so the opening(s) in skin side 6 of sample collection chamber 5 are open to the skin of the subject.

In its broadest scope, the target molecule can be any one or more transdermally emitted gas. By "gas" it is meant any molecule that at the subject's ordinary body temperature (36.5-37.5° C. for humans) escapes from the surface of the subject's uncovered skin in the form of a vapor. Note that the boiling temperature of the material may be higher than the body temperature of the subject. The gas may have a vapor pressure of at least 75 mm Hg or at least 100 mm Hg at 38° C. The method of the invention is particularly suitable for the capture and analysis of small molecules, especially those having molecular weights of up to about 100 g/mol. The target molecule can be one or more of carbon dioxide, oxygen, nitric oxide, nitric dioxide, hydrogen peroxide, acetaldehyde, carbon monoxide, ammonia, hydrogen sulfide, acetone, hydrogen cyanide and formaldehyde.

The target molecule is detected by sealably mounting at least one dermal sampling strip of the invention onto the skin of a biological subject, and collecting the transdermally emitted gas in the sample collection chamber of the dermal sampling strip(s), and analyzing for one or more target molecules. The biological subject may be a living animal, particularly a living mammal and especially a domesticated mammal or human. The biological subject may also be plant tissue, particularly a fruit, leaf, or vegetable such as apples, pears, peaches, any type of citrus fruit, bananas and other tropical fruit, melons, squash, tomatoes, peppers and the like. The "skin" of the subject is for purposes of this invention the outermost tissue layer, i.e., the epidermis of an animal and the peel, husk or shell of a fruit or vegetable.

Sealably mounting the dermal sampling strip can be accomplished in various ways. Because the skin and underlying musculature is usually somewhat soft and flexible, an adequate seal often can be obtained simply by applying sufficient pressure onto dermal sampling strip 2. Such applied pressure, such as can be applied by the subject itself or another person (who could be, for example a clinical technician). Under sufficient pressure, the skin will deform slightly and conform to the surface of skin side 6 of dermal sampling strip 2 to create a seal. Therefore, a separate sealing means may not be necessary.

Alternatively, dermal sampling strip can be secured to skin by separate means, such as, for example, a tape, gauze, sleeve, clamp, band or wrap that is applied over the dermal sampling strip and which adheres to or otherwise secures the strip to the skin such that a seal forms between the skin and the skin side of the sample collection chamber. Various surgical tapes are suitable for this purpose.

Figure 2:
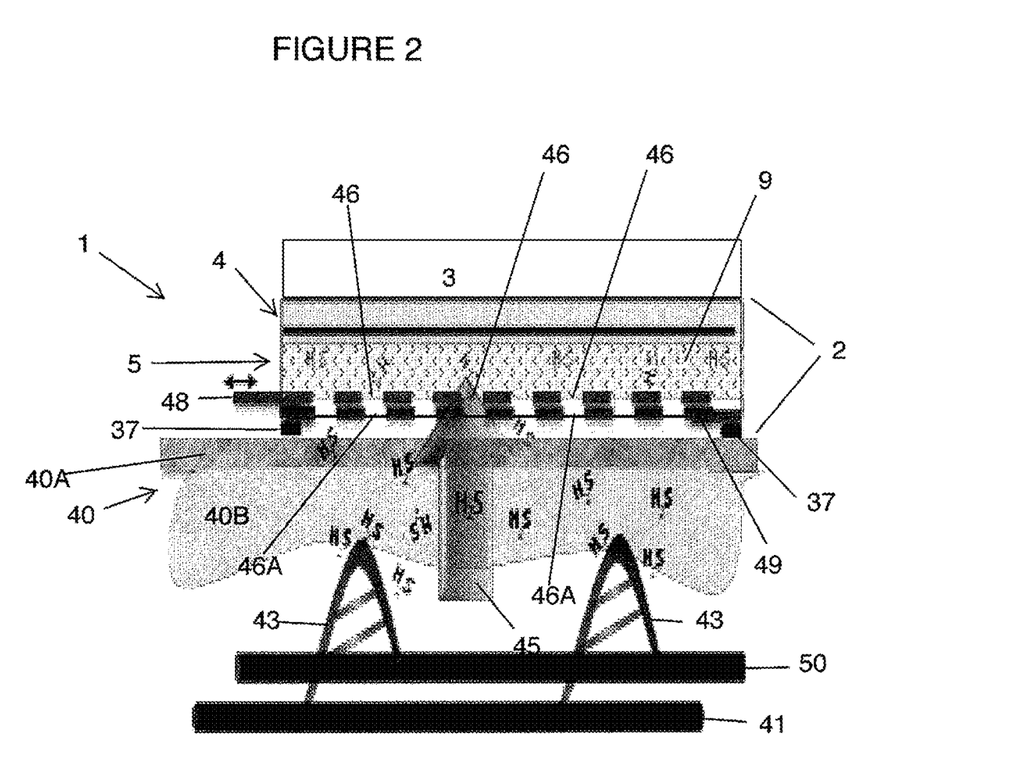
FIG. 2 is a cross-sectional side view of an embodiment of a transdermal gas analyzer of the invention, affixed to the skin of a living subject.

Alternatively, the sealing and mounting means can be incorporated into the dermal sampling strip 2 itself and/or transdermal gas analyzer 1. In the embodiment shown in FIG. 1, such sealing and mounting means includes rim 37, which is affixed to skin side 6 of peripheral walls 7 of sample collection chamber 5 of dermal sampling strip 2. In such embodiment, dermal sampling strip is sealingly mounted to the skin of the subject via direct contact between the skin 40 and rim 37, as shown in FIG. 2. By "sealingly mounted" it is meant that the dermal sampling strip is mounted to the skin of the biological subject such that gasses emitted from the skin of the subject in the area covered by the dermal sampling strip 2 are prevented from escaping the interface between the skin and the dermal sampling strip, so those gasses become captured in the vapor space of the sample collection chamber.

Rim 37 may be replaced or supplemented with alternative means for securing dermal sampling strip 2 to skin 40. One or more sleeves, clamps, bands and/or wraps that are permanently affixed to transdermal gas analyzer 1 and/or dermal sampling strip 2 may perform the necessary sealing and mounting function.

FIG. 2 illustrates an embodiment of the mounting of transdermal gas analyzer 1 of the invention onto the skin 40 of a living animal subject. Transdermal gas analyzer 1 includes dermal sampling strip 2 and electronics module 3. Dermal sampling strip 2 includes sample collection chamber 5 and detector 4. Skin contact side 6 in this embodiment includes porous plate 49 and sliding closure 48, which together define an optional feature, i.e., a recloseable skin-side opening. Porous plate 49 includes multiple openings 46A and sliding enclosure 48 includes multiple openings 46.

Sliding closure 48 is slidably mounted onto dermal sampling strip 2 along skin contact side 6. When in an open position (as shown), openings 46 align with openings 46A to create a flow path for the transmission of gasses from skin 40 into vapor space 9 of sample collection chamber 5. When moved into a closed position, openings 46 and openings 46A are no longer aligned, closing the flow paths from skin 40 into vapor space 9. Vapor space 9 of sample collection chamber 5 is thus sealed, trapping gasses emitted from skin 40 inside sample collection chamber 5. In an alternate design, sliding closure 48 lacks pores or other openings through which emitted gasses can pass. In such an alternate design, sliding closure 48 slides out of dermal sampling strip 2 to open openings 46A of porous plate 49 and create a flow path for gasses from skin 40 into vapor space 9, and can then be replaced to seal sample collection chamber 5.

Alternate recloseable openings for skin side 6 of dermal sampling strip 2 include, for example, a movable plate mounted on skin contact side 6 such that dermal sampling strip 2 is compressed, the moveable plate moves inward, forming openings 4 around some or all of the periphery of skin contact side 6 of sample collection chamber 5. Means such as springs or a flexible but resilient foam material that occupy some or all of sample collection chamber 5 are provided to return such a moveable plate to its original position when dermal sampling strip 2 is not under compression. Such a resilient foam material preferably is an open-celled (at least 50% open and interconnected cells, more preferably at least 80% open cells) foam, as to not form a diffusion barrier for transdermally emitted gases.

In the embodiment shown in FIG. 2, the means for securing dermal sampling strip 2 to skin 40 is adhesive rim 37. Adhesive rim 37 is mounted on skin contact side 6 of dermal sampling strip 2, and provides a seal between skin 40 and dermal sampling strip 2. Such seal prevents gasses emitted from skin 40 in the area covered by dermal sampling strip 2 from escaping the interface between skin 40 and dermal sampling strip 2, so that such emitted gasses pass through openings 46 and 46A into vapor space 9 of sample collection chamber 5, where they are captured. Adhesive rim 37 thus performs two functions in the embodiment shown in FIG. 2; i.e., sealing and adhesion.

As shown in FIG. 2, skin 40 includes stratum corneum 40A and viable epidermis 40B, which are supplied with blood through artery 41. Capillaries 43 transfer blood from artery 41 through viable epidermis 40B and to vein 50. Blood gasses (indicated as H$_2$S) are emitted from the blood as it traverses viable epidermis 40B and move in the general direction indicated by arrow 45, through stratum corneum 40A, openings 46 and 46A and into sample collection chamber 5, where they are captured.

In operation, dermal sampling strip 2 is applied to skin 40 and held in place via adhesive rim 37, which seals the periphery of dermal sampling strip 2 to skin 40 and prevents the escape of gasses from the interface between dermal sampling strip 2 and skin 40.

Rim 37 is optional but preferred. Rim 37 suitably is made at least in a part of an elastomeric material, preferably an elastomeric foam material such as a polyurethane, silicone or other rubbery material. Rim 37 preferably is compressible. When dermal sampling strip 2 is applied to the skin of the biological subject, rim 37 forms a seal between the skin and the sample collection chamber. Rim 37 may consist of or include an adhesive layer that bonds to the skin of the biological subject.

Once in place, sliding closure 48 is opened, aligning openings 46 and 46A and creating a flow path for gasses emitted through skin 40 into vapor space 9 of sample collection chamber 5. After gasses are collected for a period of time (the "sampling time"), sliding closure 48 is closed, sealing sample collection chamber 5. The sampling time may be measured and/or predetermined so transdermal emission rate data can be calculated.

The detection of one or more transdermally emitted gases collected in sample collection chamber 5 is performed by detector 4.

In preferred embodiments as shown in FIGS. 1 and 2, analysis for the target transdermally emitted gas is performed via a detector such as detector 4 that is mounted (permanently or removably and replaceably) onto dermal sampling strip 2. Alternatively, the captured emitted gas is transferred from the dermal sampling strip to a separate apparatus for remote analysis. This can be performed, for example, by transporting the contents of the sample collection chamber from the dermal sampling strip to a separate analytical device or into a collection vessel that is then taken for analysis. The captured gas itself can be transported in this manner. If the transdermal gas is captured on a sorbent or fixative as described above, the sorbent or fixative with the captured transdermal gas may be removed from the dermal sampling strip and taken for remote analysis. Alternatively, the entire dermal sampling strip can be taken to remote analysis.

Detection of the captured transdermally emitted gasses can be performed continuously, if the detector resides on or is mounted onto the dermal sampling strip (as shown in FIGS. 1 and 2) or the vapor space of the sample collection chamber is continuously in communication with a remote detector. More typically, however, (due to the low rates of emission of gasses through the skin) the transdermally emitted gasses are captured and permitted to concentrate in the sample collection chamber, and then taken once or periodically for analysis. Preferably, the dermal sampling strip is affixed to the skin and left in place for a predetermined and/or measured period of time. Preferably, a quantitative measurement of at least one target molecule is made. The duration of sample collection and the measured quantity of transdermally emitted gases permits a calculation of an estimated emission rate through the skin. The rate of gas emission can be used to estimate the concentration of the emitted gas in the blood.

For a gas such as H$_2$S, for example, one way of performing this estimate is through the relationship:

$$\frac{d}{dt}(n_{H_2S}) = \left(\frac{A_s}{\delta/D}\right) \cdot \left[\chi_i - \left(\frac{R \cdot T \cdot k_H}{\forall_s}\right) n_{H_2S}\right]. \quad (1)$$

wherein t is sampling time (s), $n_{H_2S}$ is moles of H$_2$S gas in the strip, $\chi_i$ is molar concentration of free H$_2$S in blood, D is diffusivity of H$_2$S through skin (reported to be approximately $6 \times 10^{-7}$ cm$^2$/s), $\delta$ is skin thickness (cm), $\forall_s$ is void volume in the strip (mL), $A_s$ is dermal surface area covered by the strip (cm$^2$), R is the Universal Gas Constant (8.314 N·m/mol-K), T is gas temperature (K), and $k_H$ is the Henry's law constant for solubility of H$_2$S in skin (mol/L-bar). One can solve Equation (1) for finding $n_{H_2S}$ (or $C_{H_2S} = n_{H_2S}/n_{air}$, gas concentration in ppm). Equation 1 can be generalized to estimate blood concentrations of other transdermally emitted gases by substituting constants applicable to the specific transdermally emitted gas.

At the t→0 asymptotic limit, the rate of gas emission through the skin is linear and is independent of the solubility of the gas in the skin. Therefore, at times close to t=0, the rate of change of the concentration of the captured gas in the sample collection chamber is indicative of $\chi_i$, the molar concentration of the free gas in the blood. Measuring the captured gas at one or more times close to t=0 therefore provides an estimate of $\chi_i$. To estimate $\chi_i$ in this manner, the sampling time may be, for example, up to 1 hour, up to 5 minutes or up to 2 minutes.

The concentration of a transdermally emitted gas in the sample collection chamber will increase over time, as long as the strip is applied to the skin and the sample collection chamber is open to the skin surface, until the concentration reaches equilibrium, or a limiting concentration of the transdermally emitted gas. This limiting concentration is indicative of the solubility of the gas in the skin. Therefore, in alternative embodiments, the sampling time is long enough that the concentration of the gas approaches or reaches the limiting concentration. The sampling time in this case may be, for example, at least 2 minutes, or at least 5 minutes. A preferred time is 15 minutes to 24 hours, depending on the particular gas and physiological conditions.

By applying a dermal sampling strip and measuring both the rate of emission of the transdermally emitted gas and the value at close to equilibrium, one can therefore obtain estimates of both the molar concentration of the gas in the blood and the solubility of the gas in the skin. Each of these parameters may be indicative or diagnostic of a particular medical condition or disease (or lack thereof), or other condition such as the presence or absence of a substance (such as a metabolize) in the subject.

In some embodiments, multiple dermal sampling strips of the invention are affixed to a subject's skin as described before and correspondingly multiple samples of transdermally emitted gas are collected simultaneously and/or serially and analyzed. For example 2 to 20, 2 to 10 or 2 to 5 dermal sampling strips may be used in such manner.

The use of multiple dermal sampling strips in this way has several potential advantages. In some instances, the captured transdermally emitted gases from multiple strips can be combined for analysis. This permits, for example, larger quantities of the transdermally emitted gas to be captured, leading to easier and often more accurate analysis. This is an important advantage, because of the very low concentrations of the transdermally emitted gases that typically are captured.

Another advantage of using multiple dermal sampling strips in this way is that the time needed for sample collection can be reduced.

The transdermally emitted gases captured in each individual dermal sampling strip can of course be analyzed for separately from those captured in the other dermal sampling strips, if desired. By doing so, one can obtain comparative rates of emission of one or more transdermally emitted gases from different parts of a subject's body. Differences in the rates of emission between different parts of the subject's body may in some instances be indicative or even diagnostic of disease and/or abnormal function, for example, blood circulation abnormality. In the case of $H_2S$ emissions, for example, a significant difference in rate between the limbs of a living animal (including a human subject) is often indicative of peripheral artery disease in one or more of the limbs. By applying dermal sampling strips to, for example, both legs and/or both arms of a subject, or to a limb and to the torso, collecting the transdermally emitted gases and analyzing for $H_2S$ emitted from each limb separately, or from the limb and torso separately, and comparing the results, one therefore can obtain an indication (or lack thereof) of peripheral artery disease. More generally, by applying multiple dermal strips symmetrically to parts of a subject's body, one can differentially detect and measure the transdermal emission of one or more gasses from, for example, opposing limbs or other symmetrical body parts. Differences in emission rates between such symmetrical body parts may be indicative of a medical condition or disease.

In 1-methylcyclopropene-treated or untreated fruits and vegetables, the emission of metabolites such as ethylene, acetaldehyde, and ethanol is indicative of ripeness and/or decay. Measuring the emission of such metabolites in accordance with this invention therefore can provide an indication of whether the fruit or vegetable is becoming ripe, and also can provide an indication of the state and/or rate of ripening. Further, fruits, vegetables, and flowers are often treated with 1-methycyclopropene (1-MCP), a synthetic molecule known as ethylene blocker, to prevent ripening. Monitoring 1-MCP on these products would facilitate determination of whether or not they can be classified as organic.

Alternatively, or in addition, the gasses captured by different sampling strips can be analyzed for different analytes ("orthogonal detection"). Orthogonal detection can be used to isolate specific abnormalities or medical conditions, or to screen for or diagnose two or more medical conditions or diseases at the same time.

The preferred method of analysis is via the electrocatalytic reaction at the working electrode of an electrochemical cell, which preferably is mounted onto the dermal sampling strip as shown in FIG. 1.

The electrocatalytic approach offers several important advantages. Electrocatalytic methods can reliably detect quantities of many target gases, particularly $H_2S$, at concentrations as low as 1 part per billion by volume in the sample collection chamber. Accordingly, sample collection times can be quite short (as little time is usually needed to achieve such concentrations of the target gas in the sample collection chamber), and reliable emission rate estimates can be made quickly and easily. The electrocatalytic detector can, through selection of particular working electrode and applied potential, be set to detect specific gasses, which often react selectively in the presence of particular working electrode metals and particular applied potentials. If two or more transdermally emitted gases react simultaneously under certain conditions, one can often achieve quantitative estimates of the amounts of each gas, by sequentially operating the cell at different potentials, at one of which only one of the transdermally emitted gas reacts. By sequentially operating the cell at different potentials, it is also possible in some cases to determine the presence and/or amounts of two or more transdermally emitted gasses from a single collected sample.

Another important advantage of the invention, particularly when electrocatalytic detection methods are used, is that it usually is not necessary to heat the skin to accelerate the transmission of gasses out of the skin and into the sample collection chamber. The ability to detect, qualitatively and/or quantitatively, very small concentrations of many transdermally emitted gases, makes it unnecessary to heat the skin or otherwise accelerate the emission rate. Therefore, sample collection preferably is performed at the body temperature of the subject (if a living animal), or at ambient temperature (in the case of fruits, vegetables and non-living subjects), without applied heating or cooling.

Still another advantage of the invention, particularly when electrocatalytic detection methods are used, is that response times tend to be on the order of seconds or even fractions of a second.

One method of detecting $H_2S$ involves a dual detection, one of $H_2S$ directly and one of $SO_2$ obtained by catalytic oxidation of the $H_2S$. In such a method, the captured transdermal gasses are removed from the sample collection chamber and split into two samples. Alternatively, two different samples are captured using two different dermal sampling strips. One of the samples is passed through an analytical device adapted to detect $H_2S$, such as an electro-catalytic sensor in which the working electrode (which may be a gold electrode) is set at a bias potential of approximately 200 mV vs. MSE. The second stream passes through a catalytic oxidation unit to convert the $H_2S$ molecules to $SO_2$. The oxidation catalyst may be, for example, a molecular sieve or $\gamma$-$Al_2O_3$ particles. The gases exiting the catalytic oxidation unit are air cooled if necessary and then analyzed for $SO_2$. An alternative method of creating a $SO_2$ stream is to pass the sample gas containing the target $H_2S$ molecules through a raw (none surface-treated or heat-treated) activated carbon fiber (ACF) matrix, which adsorbs the $H_2S$ gas and concentrates it as described by Feng et al., "Adsorption of Hydrogen Sulfide onto Activated Carbon Fibers: Effect of Pore Structure and Surface Chemistry," *Environ. Sci. Technol.* 2005, 39, 9744-9749. Once concentrated, some or all of the $H_2S$ can be thermally converted to $SO_2$. The gases are released from the ACF matrix through a temperature programmed desorption (TPD) process, releasing the different gas species at various temperatures. This process most likely creates a strong $SO_2$ peak at a temperature of 300° C. to 400° C. The $SO_2$ detector may be another electrocatalytic cell maintained at a bias potential of approximately −65 mV vs. MSE and optimized for reaction and sensing of $SO_2$ molecules.

Alternatively, the use of a heat-treated ACF (oxidation at 200° C. and heat treatment in nitrogen at 900° C.) will result in adsorption of $H_2S$ gas during the adsorption cycle, a part of which is converted to $SO_2$, and both $SO_2$ (250° C. to 300° C.) and $H_2S$ (300° C. to 350° C.) molecules are released during the TPD process. This approach would only require one detector, since both peaks are discriminated by TPD. The dual detection gives independent measurements of the $H_2S$ in sample collection chamber.

EXAMPLE

A transdermal gas analyzer as generally shown in FIG. 1 is evaluated in the detection of hydrogen sulfide. The working electrode is a gold layer deposited onto a Nafion polymer membrane. The electrolyte is a dilute sulfuric acid solution. The reference and counter electrodes are graphite. The circuitry maintains a voltage of approximately 200 mV vs. MSE across the electrocatalytic cell, and includes a potentiostat that measures current produced at the working electrode due to the catalytic reaction of hydrogen sulfide.

In a first test, a standard gas containing 1 part per million $H_2S$ is injected into vapor space 9, followed by a steady injection of a purge gas (air). The detector produces a current of about 0.017 mA in response to the injected gas. The signal decays rapidly as the test sample is replaced by the purge gas.

In a second test, test gases containing 10, 50 and 100 parts per billion (ppb) $H_2S$ are injected into vapor space 9, to simulate gas concentrations expected to be seen from a living mammal subject in a reasonably short sample time. The sensor responds by producing currents of about 0.06, 0.22 and 0.38 microamps. These results indicate a straight-line correlation of produced current to $H_2S$ concentration.

What is claimed is:

1. A method for measuring the transdermal emission of a hydrogen sulfide and/or nitric oxide through the skin of a biological subject, comprising
    a) sealably mounting multiple dermal sampling strips to skin on opposing limbs of the subject, wherein each dermal sampling strip includes a sample collection chamber that comprises (i) a skin contact side that is in contact with the skin when the dermal sampling strip is mounted and (ii) one or more walls, the skin contact side and the wall(s) together defining a vapor space for collecting transdermally emitted gas, wherein the skin contact side has one or more openings which create one or more fluid paths between the skin and the vapor space for collecting the transdermally emitted gas, and each dermal sampling strip is flexible and bends to conform to the surface of the skin to form a seal between the skin and the sample collection chamber;
    b) collecting the transdermally emitted gas in the sample collection chamber of each of the dermal sampling strips; and
    c) separately analyzing for the presence of hydrogen sulfide and/or nitric oxide in the transdermally emitted gas collected in the sample collection chamber of each of the dermal sampling strips and obtaining differential rates of emission of hydrogen sulfide and/or nitric oxide transdermally emitted through the skin of each of the opposing limbs by separately contacting the transdermally emitted gas collected in the sample collection chamber of each of the dermal sampling strips with a working electrode of an electrocatalytic cell, and measuring an electrical signal created by a reaction of hydrogen sulfide and/or nitric oxide in the transdermally emitted gas at the working electrode, the working electrode forms or is mounted onto at least one of the walls of the sample collection chamber and further wherein the hydrogen sulfide and/or nitric oxide in the transdermally emitted gas is transported from the skin to the working electrode without passing through a diffusion barrier.

2. The method of claim 1 wherein the working electrode is in fluid communication with the vapor space sample collection chamber.

3. The method of claim 1, wherein the reaction of the hydrogen sulfide and/or nitric oxide in the transdermally emitted gas at the working electrode creates an electrical signal that indicates the qualitative and/or quantitative presence of said hydrogen sulfide and/or nitric oxide in the transdermally emitted gas in the vapor space of the sample collection chamber and the dermal sampling strip further includes or is in electrical connection with means for detecting and/or measuring said current.

4. The method of claim 1 wherein the biological subject is a living human.

* * * * *

UNITED STATES PATENT AND TRADEMARK OFFICE
CERTIFICATE OF CORRECTION

| | |
|---|---|
| PATENT NO. | : 12,053,281 B2 |
| APPLICATION NO. | : 16/952300 |
| DATED | : August 6, 2024 |
| INVENTOR(S) | : Alireza Shekarriz and Debra May Friedrichsen |

It is certified that error appears in the above-identified patent and that said Letters Patent is hereby corrected as shown below:

In the Specification

After the title, please insert:
--STATEMENT OF GOVERNMENT SUPPORT
This work was made with government support under contract no. HL121871 awarded by the United States National Heart, Lung and Blood Institute. The United States Government has certain rights to this invention.--

Signed and Sealed this
Twenty-ninth Day of October, 2024

Katherine Kelly Vidal
*Director of the United States Patent and Trademark Office*